United States Patent [19]

Zupancic et al.

[11] Patent Number: 5,387,656
[45] Date of Patent: Feb. 7, 1995

[54] SUBSTITUTED CYANOGUANIDINES AS CURING AGENTS FOR EPOXY RESINS

[75] Inventors: Joseph J. Zupancic, Bensenville; Jeffrey P. Conrad, Chicago, both of Ill.

[73] Assignee: AlliedSignal Inc., Morris Township, Morris County, N.J.

[21] Appl. No.: 153,401

[22] Filed: Nov. 16, 1993

Related U.S. Application Data

[63] Continuation-in-part of Ser. No. 912,045, Jul. 19, 1992, abandoned, which is a continuation of Ser. No. 557,445, Jul. 23, 1990, abandoned.

[51] Int. Cl.$^6$ .............................................. C08L 63/02
[52] U.S. Cl. ................................. 525/523; 525/527; 564/104
[58] Field of Search ........................ 525/523; 564/104

[56] References Cited

U.S. PATENT DOCUMENTS

| | | | |
|---|---|---|---|
| 2,455,807 | 12/1948 | Redmon et al. | 260/551 |
| 2,455,894 | 12/1948 | Lecher et al. | 564/104 |
| 3,391,113 | 7/1968 | Lopez et al. | 260/47 |
| 3,553,166 | 1/1971 | Anderson et al. | 260/47 |
| 3,734,868 | 5/1973 | Uelzmann et al. | 260/2.5 AM |
| 4,311,753 | 1/1982 | Pucci | 428/251 |
| 4,560,690 | 12/1986 | Reiter | 514/256 |
| 4,581,422 | 4/1986 | Speranza et al. | 525/504 |

FOREIGN PATENT DOCUMENTS

| | | | |
|---|---|---|---|
| 503136 | 5/1954 | Canada | 564/104 |
| 0306451 | 8/1988 | European Pat. Off. | |
| 0310545 | 8/1988 | European Pat. Off. | |
| 61-207425 | 9/1986 | Japan | |
| 577843 | 5/1944 | United Kingdom | |
| 599713 | 3/1948 | United Kingdom | 564/104 |

OTHER PUBLICATIONS

May, Everette, "Attempts to Find New Antimalarials, XXI, Guanidine and Biquanide Derivatives of Phenanthrene" J. Org. Chem. 12 (1947) pp. 437–445.

Curd, F. H. S. and rose, F. L., "Synthetic Antimalarials, Part X, Some Aryldiguanide (-biguanide) Derivatives" J. Chem. Soc. 729–737 (1946).

Curd, Henry, Kenny, Murray and Rose "Synthetic Antimalarials, Part XXVIII. An Alternative Route to $N^1$–Aryl–$N^5$ alkyldiguanides" J. Chem. Soc. 1630–1636 (1948).

*Primary Examiner*—Robert E. Sellers
*Attorney, Agent, or Firm*—Harold N. Wells; Mary Jo Boldingh; Roger H. Criss

[57] ABSTRACT

A curing agent for epoxy resins having improved solubility characteristics has the formula $$\text{RNH}-\overset{\overset{\displaystyle \text{NCN}}{\|}}{\text{C}}-\text{NH}_2$$

where R is —$CH_2C_6H_4X$ or —$CH_2CH_2C_6H_4X$, and X is either —H, —$CH_3$, —$OCH_3$, —OH, or —NY, and where Y is —H or $CH_3$.

Such substituted cyanoguanidines are soluble in various solvents and do not require the use of undesirable solvents necessary with cyanoguanidine (dicyanodiamide) itself.

11 Claims, No Drawings

SUBSTITUTED CYANOGUANIDINES AS CURING AGENTS FOR EPOXY RESINS

CROSS-REFERENCE TO RELATED APPLICATIONS

This is a continuation-in-part of application Ser. No. 07/912,045 filed Jul. 19, 1992 which is a continuation of Ser. No. 07/557,445 filed Jul. 23, 1990, both now abandoned.

The invention relates generally to the curing of epoxy resins and, more particularly, to improvement of the curing agents used with epoxy resins. Dicyanodiamide (also called cyanoguanidine) is well-known as a curing agent for epoxy resins and replacing it with an improved curing agent has been an objective of the present inventors.

PRIOR ART

Dicyanodiamide is well-known as a latent curing agent for epoxy resins but it is also known to have a serious deficiency. It is only soluble in solvents which are undesirable, either because they are not usable in most applications, such as water, or the solvents are relatively expensive and environmentally undesirable, such as dimethylformamide and the like.

In U.S. Pat. No. 3,553,166 a curing agent is disclosed which combines a metal salt of an imidazole and another compound, which may be dicyanodiamide. These curing agents are used in a one-part epoxy composition which is curable at elevated temperatures, but which can be stored at ambient temperature for long periods.

Another combination of dicyanodiamide with a second compound is found in U.S. Pat. No. 4,311,753 where dicyanodiamide is combined with tetraalkyl guanidine to provide a curing agent for mixtures of di- and tetra-functional epoxides. The use of tetraalkyl guanidines is shown in U.S. Pat. No. 3,391,113 to have the effect of lowering the curing temperature of dicyanodiamide, which is said to require a temperature above about 160° C., preferably about 215° C.

The reaction product of dicyanodiamide with formaldehyde and an amine terminated polyether may be used to cure epoxy resins, as is shown in U.S. Pat. No. 4,581,422. Such a product is a substituted cyanoguanidine, but by adding an amine terminated polyether and a methylene group from the formaldehyde it differs from those of the present inventors, as will be seen below.

A somewhat similar composition is disclosed in Japanese published patent application 61-207425 which employs a two-part system using as one part an epoxy hardener combining cyanoguanidine compounds, polyether polyamines, and guanidine compounds. Although substituted cyanoguanidine compounds were disclosed, the patentees made it clear that their three component hardening composition was directed to the problems associated with the poor solubility of dicyandiamide. A two-part composition was needed to provide adequate shelf life and to avoid the curing effect at ambient temperatures which one would expect from addition of a polyether polyamine to act as a reactive diluent and dispersant for the insoluble dicyandiamide.

Two recent published European patent applications cover certain substituted cyanoguanidines said to be useful as curing agents for epoxy resins. In EP 306,451 oligomers of substituted 3-cyanoguanidines are discussed. Such compounds are produced by the reaction of a monoisocyanate with a diisocyanate to form the oligomer, followed by reaction with cyanamide to form compounds having the formula:

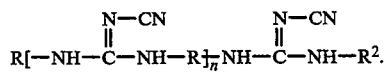

These compounds differ from those of the present inventors in that they are oligomers and both the terminal amino groups are substituted, thus reducing the functionality of these compounds. The applicants recognized the problem discussed above which is inherent with the use of dicyanodiamide, namely, the need to use objectionable solvents. The new oligomeric cyanoguanidines are said to dissolve well in suitable solvents and to produce epoxy resins having a high glass transition temperature. Another published application is EP 310,545 in which di-substituted cyanoguanidines having the formula:

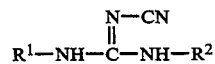

are said to be useful as curing agents for epoxy resins. These substituted cyanoguanidines are prepared by reacting a disubstituted carbodiimide ($R^1$—N=C=N—$R^2$) with cyanamide ($NH_2C$=N). As with the compounds of EP 306,451, these di-substituted cyanoguanidines are substituted at both the amine groups.

Substituted cyanoguanidines have also been suggested as being useful in the preparation of polyurethanes as shown in U.S. Pat. No. 3,734,868.

Related materials have also been used as precursors to various pharmaceuticals, an example of which is U.S. Pat. No. 4,560,690.

U.S. Pat. No. 2,455,807 is relevant to a preferred method of preparing the substituted cyanoguanidine compounds of the present invention. The reaction of dicyanamide with the desired substituted amine is shown to produce the substituted cyanoguanidine.

SUMMARY OF THE INVENTION

A latent curing agent for curing epoxy resins at temperatures above ambient and having improved solubility characteristics relative to dicyandiamide is found in monosubstituted cyanoguanidines having the formula:

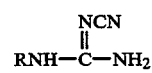

where R is —$CH_2C_6H_4X$, or —$CH_2CH_2C_6H_4X$
and X is either —H, —$CH_3$, —$OCH_3$, —OH, or —$NY_2$
and Y is —H or —$CH_3$.

Such monosubstituted cyanoguanidines are soluble in various solvents such as acetone, methyl ethyl ketone, methyl isobutyl ketone, and cyclohexanone. In service as curing agents the substituted cyanoguanidines will be employed in amounts up to about 20 wt. % of the epoxy resin precursors, preferably 2 to 10 wt. %.

In another aspect, the invention is a method for curing epoxy resins at temperatures above ambient in which a reactive amount of a substituted cyanoguanidine as defined above is added to an epoxy resin precursor in amounts up to about 20 wt. %, preferably 2 to 10 wt. %, optionally with a catalyst such as an imidazole or amine compound, and the curing carried out under curing conditions.

DESCRIPTION OF THE PREFERRED EMBODIMENTS

It has been recognized that dicyanodiamide (i.e. cyanoguanidine), although widely used, is an undesirable curing agent for epoxy resins, since it requires the use of objectionable solvents such as dimethylformamide and the like. Dicyandiamide is a latent curing agent as compared with curing agents such as aliphatic amines, polyether polyamines such as diethylene glycol bispropylamine, diethylenetriamine, triethylenetetramine, etc. which are able to cure epoxy resins at ambient temperatures. One-part epoxy resin compositions become possible with latent curing agents. Those curing agents which are reactive at ambient temperatures normally are kept separated from the epoxy resin until curing is wanted.

If more soluble compounds could be found which provide equivalent or improved curing properties, then dicyandiamide could be replaced and the undesirable solvents avoided. Reduced production costs from the use of less expensive solvents also could be the result of such a change in curing agents. The present inventors have investigated potential curing agents and have found certain substituted cyanoguanidines which have significant advantages over the parent compound, being soluble in both more desirable solvents such as acetone and neat epoxy resins.

Composition of Substituted Cyanoguanidines

Mere substitution of other groups for the hydrogen atoms in cyanoguanidine (i.e. dicyanodiamide) is not sufficient to provide the desired results. As will be seen, many substituted cyanoguanidines do not have the improved solubility characteristics sought. Further, substitution of both of the amino groups of cyanoguanidine that is, compounds of the generic formula:

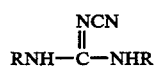

such as are shown in EP 310,545 are less satisfactory, as will be shown below.

The inventors have found that monosubstituted cyanoguanidines having the formula

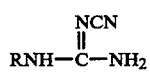

where R is —$CH_2C_6H_4X$, or —$CH_2CH_2C_6H_4X$
and X is either —H, —$CH_3$, —$OCH_3$, —OH, or —$NY_2$
and Y is —H or —$CH_3$
have improved solubility over the parent compound and still retain a high curing ability so that they are effective in amounts of up to about 20 wt. percent, preferably 2 to 10 wt. percent, of the epoxy resin precursors.

The monosubstituted cyanoguanidines of this invention and the di-substituted cyanoguanidines of EP 310,545 differ in the degree of reactive functionality. In order for the curing agent to react and generate a cross-linked epoxy based polymer network, the amine radicals react with the epoxide radicals. The degree of reactive functionality of the cyanoguanidine will depend on the degree of functionalization for the cyanoguanidine, which is related to the number of exchangeable nitrogen hydrogens of the cyanoguanidine. For example, dicyanodiamide (cyanoguanidine) has a defined degree of functionality of four, that is, it is capable of addition to four epoxide radicals. In the case of a mono-substituted cyanoguanidine the degree of functionality is three and it is capable of reacting with three epoxide radicals. For a di-substituted cyanoguanidine as in EP 310,545 the degree of functionality is two, and it is capable of reacting with two epoxide radicals.

The degree of reactive functionality for the curing agent will affect the type of polymer network formed in the cured polymer system and consequently will affect the performance properties in B-Stage or a prepreg such as the viscosity as a function of cure, the solvent resistance for the polymer, the glass transition temperature (Tg) for the polymer, and the coefficient of thermal expansion ($a_g$). For example, when a curing agent with a degree of reactive functionality of two (EP 310,545) is employed, the network will have a high degree of linear structures with only a minor degree of branching. When a curing agent with a degree of reactive functionality of three (the present invention) is employed, the polymer network will have a high degree of branched or star-like structures and a minimum of linear type structures. The branched or star-like structures will affect the resin flow properties (resin flow viscosity) for the B-Staged resin during lamination. If the resin flow viscosity is low, then the laminates or composites formed will experience a high degree of resin flow, generating laminates or composites with voids or resin-poor products. Linear structures in the cured polymer will yield poor solvent resistance due to the solvation of the polymer fragments or swelling of the polymer. Branched or star-like structures provide improved solvent resistance due to the formation of a more highly cross-linked network. Linear structures will yield a polymer of lower Tg and may yield higher coefficient of thermal expansion than a polymer with branched structures.

Solvents

The parent compound, cyanoguanidine, is soluble only in a small group of generally available solvents, including dimethylformamide, dimethylsulfoxide, dimethylacetamide, N-methyl-2-pyrrolidinone and methanol. The monosubstituted cyanoguanidines of the invention are soluble in a number of more desirable solvents, including acetone, methyl ethyl ketone, methyl isobutyl ketone, cyclohexanone, methanol, ethanol, or neat epoxy resins. It is their potential use in solvent-free epoxy resin formulations, or those including only small amounts of solvents which is a particularly attractive commercial prospect for the substituted cyanoguanidines of the invention. In particular, acetone, methyl ethyl ketone, methyl isobutyl ketone, and cyclohexanone are preferred solvents.

The compounds of the invention are generally soluble in amounts up to about 45 wt. % in such solvents. In many cases the desired amount of the substituted cyanoguanidine is dissolved in enough solvent to make a solution containing about 13 to 45 wt. % of the compound and thereafter the solution is mixed with the epoxy precursors and cured under curing conditions. As pointed out above the use of solvents may be much reduced or even eliminated with the curing agents of the invention.

Epoxy Resins

The substituted cyanoguanidines of the invention may be used with various epoxy resin known in the art. In general, these will include diglycidyl bisphenol-A (DGEBA), diglycidyl tetrabromobisphenol-A, triglycidyl triphenol methane, triglycidyl triphenol ethane, tetraglycidyl tetraphenolethane, tetraglycidyl methylene dianiline, chain-extended diglycidyl bisphenol-A based on bisphenol-A and/or tetrabromobisphenol-A, and oligomers and mixtures thereof. More particularly, diglycidyl bisphenol-A (DGEBA) types and chain-extended versions have been found to provide suitable results with the curing agents of the invention.

Catalyst for Epoxy Resins

In order to facilitate the reaction of the substituted cyanoguanidine with the epoxy resin it may prove useful to employ a catalyst. There are various catalyst known in the art which can be employed. The catalyst which we believe offer distinct advantages over others will be free of transition metals. Preferred catalysts are imidazoles, including imidazole, 2-methylimidazole, 2-phenylimidazole, 1-cyanoethyl-2-phenylimidazole, 1-(2-cyanoethyl)-2-ethyl-4-methylimidazole, 4-phenylimidazole, 2-ethylimidazole, 2-ethyl-4-methylimidazole, or amines including benzyldimethylamine, 4-(dimethylamino)-N,N-dimethylbenzylamine, 4-methoxy-N,N-dimethylbenzylamine, 4-methyl-N,N-dimethylbenzylamine, 1,1'-carbonyldiamidazole, and the like.

Preparation of Laminates

An advantage of the substituted cyanoguanidines of the invention is their ability to replace the cyanoguanidine (dicyanodiamide) commonly used to cross-link epoxy resins in the preparation of reinforced laminates for the electronics industry and without requiring the use of undesirable solvents. The methods used to prepare such laminates are well known to those skilled in the art and need not be discussed in detail here in connection with the present invention since the procedures are not revised to accommodate the substituted cyanoguanidines of the invention. In general, it may be stated that the fabric which is to be used to reinforce the laminate, typically made of glass fibers, is coated with epoxy resins combined with the crosslinking agents and a catalyst as desired. The epoxy resin composition is a one-part mixture in contrast to a two-part mixture often used for some epoxy resin applications where rapid ambient temperature curing is necessary. The coated fabric is then heated in order to drive off solvents and to cure (polymerize and crosslink) the epoxy resins and the crosslinking agents at above ambient temperatures. Multiple layers of coated fabric are commonly combined to provide the laminates needed for electronic circuit boards. When only a partial cure is carried out by heating to about 150°–170° C., the resulting product is often referred to as a "prepreg" or "B-stage" material. Further curing at higher temperatures, about 170°–180° C., is later carried out to complete the laminate. These processes are carried out in batch or continuous processes familiar to those skilled in the art.

Preparation of the Substituted Cyanoguanidines

The curing agents of the invention may be prepared by various methods known to those skilled in the art. For example, the method of May (J. Org. Chem., 12, 437–442, 442–445 (1947)) and Curd (J. Chem. Soc., 1630–1636 (1948)) reaction of an aryl isothiocyanate with sodium cyanamide, followed by reaction with methyl iodide to generate a N-cyano-S-methyl-N'-arylisothiourea which upon reaction with ammonia yields a substituted cyanoguanidine. Another method of Curd (J. Chem. Soc., 729–737 (1946))) and Rose (Brit. Patent 577,843) employs the reaction of an aryl diazonium salt with dicyanodiamide to yield a substituted aryl-azo-dicyanodiamide or triazene which thermally decomposes to yield nitrogen and the corresponding substituted cyanoguanidine.

Retro-Synthetic analysis of substituted dicyanodiamides indicates that the synthesis of these materials should be possible from the reaction of parent compound dicyanodiamide and an arylalkylhalide. This route would employ an aprotic solvent (such as N-methylpyrrolidinone) which is capable of dissolving dicyanodiamide and a two to four-fold of excess of dicyanodiamide. An anion of dicyanodiamide would be generated by addition of sodium or potassium hydride yielding the corresponding sodium or potassium salt of dicyanodiamide and an excess of free dicyanodiamide. Then, to this reaction medium (at 60° to 120° C.) would be added an arylalkylhalide such as benzylchloride which will yield N-Benzyldicyanodiamide. The excess dicyanodiamide would then be removed from the product and reused.

The method disclosed by Redmon et al. in U.S. Pat. No. 2,455,807 is particularly useful. This method may be described generically by the following reaction according to Redmon et al.

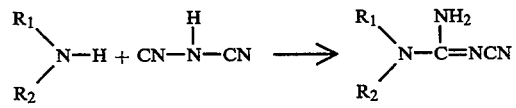

In practice, a metal salt of dicyanamide (CN—N-H—CN) preferably is used, such as sodium dicyanamide. The selected substituted amine, for example, benzyl amine may be dissolved in a suitable solvent, such as butanol, ethanol, propanol and water, or mixed with hydrochloric acid to form a slurry. Sodium dicyanamide is added in an approximately stoichiometric quantity. The reaction is carried out at temperatures between about 75° and 110° C. and at pressures of atmospheric to 2068 kPa for a period of time necessary to complete the reaction. Preferably, a temperature of about 100° to 130° C. will be used with the reaction time being about 30 minutes to 24 hours. Thereafter, if used, the solvent is distilled off and the substituted cyanoguanidine is recovered by crystallization and washing. If hydrochloric acid is used, the solids are filtered, washed, and then redissolved and crystallized from solution.

EXAMPLE 1

Synthesis of N-Benzyl-dicyanodiamide (BZDICY)

196.20 g (1.830 moles) of benzylamine and ca. 1560 mL of butanol are charged into a 5 liter 3-neck round bottom flask equipped with condenser, addition funnel and mechanical stirrer. To this stirred reaction mixture is added 100.56 g (55.0 mL, 1.020 moles) of concentrated sulfuric acid in 400 mL of butanol dropwise, final pH is 7 to 8. To the above reaction mixture is added 182.57 g (2.050 moles) of sodium dicyanamide and 40 mL of water, the reaction mixture is heated with stirring to 100° C. and maintained at 100° C.±5° C. for 6.5 hrs, during the course of the reflux 95 mL of water is added to the reaction. To the cooled reaction mixture is added an excess of water (3 liters), the butanol is azeotropically distilled off. Upon cooling a precipitate separates from the oil, which is filtered off and then washed with 1000 mL of 5% sodium hydroxide solution, filtered, washed with 1000 mL of 5% acetic acid solution, filtered and washed with 1000 mL of water. The white crystalline solid is then recrystallized from boiling water, yielding 195.8 g (61.4% yield) of white crystalline product, m.p. 109°–110° C. (Lit. m.p. 108°–109° C.); Elemental Analysis, Found C 61.99%, H 6.08%, N 30.57% Calculated C 62.04%, H 5.80%, N 32.16%.

EXAMPLE 2

Synthesis of N-Benzyl-Dicyanodiamide (BZDICY)

490.5 g (500 mL, 4.58 moles) of benzylamine is charged into a 5 liter 3-neck round bottom flask equipped with condenser, addition funnel and mechanical stirrer. To the stirred, chilled (2°–5° C.) benzylamine is added 448.9 g (378 mL, 4.58 moles) of concentrated hydrochloric acid, at a rate that insures that the reaction mixture does not exceed 50° C. The reaction slurry is heated to 75° C. and then 428.2 g (4.81 moles) of sodium dicyanamide is added and the reaction mixture is heated with stirring to 100° C. and maintained at 100° C.±5° C. for 6.5 hrs. Add 1.5 liters of water to the stirred reaction mixture and allow to cool overnight. The reaction mixture is filtered and then rinsed with 1.5 liter of water. The crystalline product is stirred with 1.77 liters of 5% sodium hydroxide solution for 2.0 hrs, filtered, rinsed with 1.77 liter of water, stirred with 1.77 liters of 5% acetic acid solution, filtered and washed with 2.5 liters of water. The white crystalline solid is then dissolved in 1.6 liter of methanol and filtered to remove any insoluble material, the methanol solution is added to 8.0 liters of water and then filtered, yielding 472.9 g (59.7% yield) of white crystalline product, m.p. 107°–109° C.

EXAMPLE 3

Synthesis of N-(4-Methylbenzyl)-dicyanodiamide (MBZDICY)

200.00 g (1.650 moles) of 4-methylbenzylamine and ca. 1400 mL of butanol are charged into a 5 liter 3-neck round bottom flask equipped with condenser, addition funnel and mechanical stirrer. To this stirred reaction mixture is added 90.65 g (50.0 mL, 0.924 moles) of concentrated sulfuric acid in 370 mL of butanol dropwise. To the above reaction mixture is added 164.57 g (1.850 moles) of sodium dicyanamide and 37 mL of water, the reaction mixture is heated with stirring to 100° C. and maintained at 100° C.±5° C. for 4.75 hrs, during the course of the reflux 85.00 mL of water is added to the reaction. To the cooled reaction mixture is added an excess of water (3 liters), the butanol is azeotropically distilled off. Upon cooling a precipitate separates from the oil, which is filtered off and then washed with 1000 mL of 5% sodium hydroxide solution, filtered, washed with 1000 mL of 5% acetic acid solution, filtered and washed with 1000 mL of water. The white crystalline solid is then recrystallized from boiling water, yielding 168.3 g (54.1% yield) of white crystalline product, m.p. 137°–138° C.; Elemental Analysis, Found C 62.84%, H 6.26%, N 29.16%, Calculated C 63.79%, H 6.44%, N 29.77%.

EXAMPLE 4

Synthesis of N-(4-Methoxybenzyl)-dicyanodiamide (MOBZDICY)

200.00 g (1.460 moles) of 4-methoxybenzylamine and ca. 1230 mL of butanol are charged into a 5 liter 3-neck round bottom flask equipped with condenser, addition funnel and mechanical stirrer. To this stirred reaction mixture is added 80.08 g (43.5 mL, 0.816 moles) of concentrated sulfuric acid in 330 mL of butanol dropwise. To the above reaction mixture is added 145.38 g (1.630 moles) of sodium dicyanamide and 32 mL of water, the reaction mixture is heated with stirring to 100° C. and maintained at 100° C.±5° C. for 6.0 hrs., during the course of the reflux 76 mL of water is added to the reaction. To the cool ed reaction mixture is added an excess of water (3 liters), the butanol is azeotropically distilled off. Upon cooling a precipitate separates from the oil, which is filtered off and then washed with 1000 mL of 5% sodium hydroxide solution, filtered, washed with 1000 mL of 5% acetic acid solution, filtered and washed with 1000 mL of water. The white crystalline solid is then recrystallized from boiling water, yielding 103.8 g (34.8% yield) of white crystalline product, m.p. 91°–93° C.; Elemental Analysis, Found C 58.62%, H 6.06%, N 26.58%, Calculated C 58.80%, H 5.93%, N 27.44%.

EXAMPLE 5

Synthesis of 4-(N,N-Dimethylamino)benzylamine 74.62 g (0.500 mols) of N,N-dimethylaminobenzaldehyde, 6.1815 g of Raney Nickel, and 200 mL of ethanol were charged into a glass liner for an 850 cc autoclave. The glass liner is placed within an autoclave and then 10.0 g of ammonia and 850 psi hydrogen at 25° C. The reactor is then heated to 70° C. over a 1.5 hour period and maintained at 70° C. for 5 hrs. The reaction mixture is then allowed to cool to ambient temperature. The reaction mixture is filtered through a fritted glass filter to remove the catalyst; and the filtrate is concentrated under vacuum to yield a yellow liquid (crude yield 73.53 g, 97.9%)

Three comparable reaction runs were combined (crude yields of 73.53 g, 88.60 g. and 76.93 g) and vacuum distilled to yield a colorless liquid of 183.0 g (81.2%), b.p. 125° C./2.4 mm (Lit. b.p. 158°–159° C./25 mm).

Synthesis of N'-4-(N,N-Dimethylamino)benzyl)dicyanodiamide (DMABZDICY)

61.4 g (0.408 moles) of 4-(N,N-dimethylamino)benzylamine and ca. 310 mL of butanol are charged into a 2 liter 3-neck round bottom flask equipped with condenser, addition funnel and mechanical stirrer. To this stirred reaction mixture is added 22.43 g (12.2 mL, 0.229 moles) of concentrated sulfuric acid in 90 mL of butanol dropwise. To the above reaction mixture is added 40.72 g (0.457 moles) of sodium dicyanamide and 10 mL of water, the reaction mixture is heated with stirring to 100° C. and maintained at 100° C.±5° C. for 5.5 hrs., during the course of the reflux 20 mL of water is added to the reaction. To the cooled reaction mixture is added an excess of water (1 liter), the butanol is azeotropically distilled off. Upon cooling a precipitate separates from the oil, which is filtered off and then washed with 300 mL of 5% sodium hydroxide solution, filtered, washed with 300 mL of 5% acetic acid solution, filtered and washed with 500 mL of water. The crystalline solid is then recrystallized from ethanol: water (90:10), yielding 55.2 g (62.3% yield) of gray crystalline product, m.p. 137°–139° C.; Elemental Analysis, Found C 61.41%, H 7.29%, N 32.34%, Calculated C 60.79%, H 6.97%, N 32.24%.

EXAMPLE 6
(Comparative)

Synthesis of N-Hexyl-dicyanodiamide (HXDICY)

153.2 g (1.51 moles) of hexylamine is charged into a 5 liter 3-neck round bottom flask equipped with condenser, addition funnel, mechanical stirrer and cooled to 5° C. via an ice bath. To this stirred reaction mixture is added 145.65 g (124.0 mL, 1.51 moles) of concentrated hydrochloric acid dropwise. To the above reaction mixture is added 133.44 g (1.50 moles) of sodium dicyanamide, the reaction mixture is heated with stirring to 100° C. and maintained at 100° C.±5° C. for 5.0 hrs, 500.0 mL of water is added to the reaction, a waxy solid forms. Upon cooling the solid is acidified with concentrated hydrochloric acid. The crystalline product is filtered and washed with water twice. Filtration and drying yields 224.5 g (89.0% yield) of white crystalline product, m.p. 95°–98° C.; Elemental Analysis, Found C 55.92%, H 8.78%, N 33.15%, Calculated C 57.10%, H 9.60%, N 33.30%.

EXAMPLE 7
(Comparative)

Synthesis of N-Dodecyl-dicyanodiamide (DDDICY)

185.36 g (1.00 moles) of dodecylamine and ca. 400 mL of butanol are charged into a 5 liter 3-neck round bottom flask equipped with condenser, addition funnel and mechanical stirrer. To this stirred reaction mixture is added 49.04 g (26.60 mL, 0.500 moles) of concentrated sulfuric acid in 50 mL of water dropwise, final pH is 6 to 7. To the above reaction mixture is added 99.71 g (1.12 moles) of sodium dicyanamide, the reaction mixture is heated with stirring to 95°–100° C. under a mild vacuum to remove water via a Dean-Stark trap, 50 mL of additional water are added and removed over 4 hrs, and maintained at 100° C.±5° C. for 3.0 Hrs. Upon cooling a precipitate separates from the oil, which is filtered off and then washed with 1000 mL of 5% sodium hydroxide solution, filtered, and then washed with water. The crystalline product is dissolved in hot ethanol, neutralized with acetic acid solution, filtered and then water added until precipitate forms. Filtration and drying yields 194.2 g (76.9% yield) of white crystalline product, m.p. 89°–90.5° C.; Elemental Analysis, Found C 66.60%, H 11.69%, N 20.77%, Calculated C 66.60%, H 11.20%, N 22.20%.

EXAMPLE 8
(Comparative)

Synthesis of N-(3-Methoxyphenyl)-dicyanodiamide (m-MOPDICY)

181.62 g (2.04 moles) of sodium dicyanamide, 400 mL of water and 246.32 g (2.00 moles) of m-anisidine are charged into a 2 liter 3-neck round bottom flask equipped with condenser, addition funnel and mechanical stirrer. The reaction mixture is heated with stirring to 100° C. and 166.0 mL of concentrated hydrochloric acid diluted with 150 mL of water is added to the reaction dropwise over an 2.5 hour interval. The reaction is maintained at 100° C. during the addition of hydrochloric acid, after addition is complete the reaction was maintained at 95°–100° C. for 3.0 hrs. A precipitate separates, which is filtered and washed with 1000 mL of water. The brown solid is then washed in methanol, yielding 295.6 g (99.7% yield) of a light pink product, m.p. 186°–188° C.; Elemental Analysis, Found C 56.27%, H 5.33%, N 29.75%, Calculated C 56.82%, H 5.31%, N 29.46%.

EXAMPLE 9
(Comparative)

Synthesis of N-Phenyl-dicyanodiamide (PDICY)

200.00 g (1.540 moles) of aniline hydrochloride and 425 mL of water are charged into a 1 liter 3-neck round bottom flask equipped with condenser, and mechanical stirrer. To the above reaction mixture is added 140.00 (1.570 moles) of sodium dicyanamide, the reaction mixture is heated with stirring to 90° C. and maintained at 90° C.±5° C. for 0.5 Hrs. A large amount of solid precipitate forms and stirring becomes ineffective, 400 mL of water is added and the reaction is maintained at temperature for 1.0 Hr. The reaction mixture is cooled and filtered and washed with 1000 mL of water. After drying 211.7 g (86.0% yield) of a grey solid product is isolated, m.p. 192°–193° C. (Lit. m.p. 194°–195° C.); Elemental Analysis, Found C 60.04%, H 5.31%, N 35.74%, Calculated C 59.98%, H 5.04%, N 34.98%.

EXAMPLE 10
(Comparative)

Synthesis of N-(4-Methylphenyl)-dicyanodiamide (p-MPDICY)

181.62 g (2.04 moles) of sodium dicyanamide, 400 mL of water and 214.32 g (2.00 moles) of p-toluidine are charged into a 5 liter 3-neck round bottom flask equipped with condenser, addition funnel and mechanical stirrer. The reaction mixture is heated with stirring to 90° C. and 192.4 g of concentrated hydrochloric acid diluted with 150 mL of water is added to the reaction dropwise over an 1 hour interval. The reaction is maintained at 100° C. during the addition of hydrochloric acid, after addition is complete the reaction was maintained at 90° C.±5° C. for 3.0 Hrs., during which a large amount of brown precipitate separates, which is filtered off and then washed with 1000 mL of 5% sodium hydroxide solution, filtered, washed with 1000 mL of 5% acetic acid solution, filtered and washed with 1000 mL of water. The solid is then washed in boiling methanol, yielding 254.2 g (72.9% yield) of white crystalline product, m.p. 211°–213.5° C. (Lit. m.p. 217°–218° C.); Elemental Analysis, Found C 62.00%, H 6.36%, N 30.81%, Calculated C 62.04%, H 5.80%, N 32.16%.

EXAMPLE 11
(Comparative)

Synthesis of N-(3-Methylphenyl)-dicyanodiamide (m-MPDICY)

168.90 g (1.90 moles) of sodium dicyanamide, 375 mL of water and 199.80 g (1.86 moles) of m-toluidine are charged into a liter 3-neck round bottom flask equipped with condenser, addition funnel and mechanical stirrer. The reaction mixture is heated with stirring to 90° C. and 154.5 mL of concentrated hydrochloric acid diluted with 125 mL of water is added to the reaction dropwise over an 2.25 hour interval. The reaction is maintained at 95° C. during the addition of hydrochloric acid. A grey solid precipitates, which is filtered off and then washed in boiling methanol, yielding 253.9 g (78.0% yield) of a grey product, m.p. 198°–201° C.; Elemental Analysis, Found C 61.99%, H 5.93%, N 31.84%, Calculated C 62.04%, H 5.80%, N 32.16%.

EXAMPLE 12

Synthesis of N-(4-hydroxybenzyl)-dicyanodiamide (HBZDICY)

36.45 g of 4-hydroxybenzylamine sulfate (0.106 mol) is slurried with 125 mL of butanol in a 500 mL 3-necked round bottom flask fitted with a Dean-Stark trap and a heating mantle. The mixture is neutralized with dilute aqueous sodium hydroxide. 91.9 g of sodium dicyanamide is then added with stirring and the temperature raised to 105° C. The temperature is maintained at 105° C. for 4.75 hours. No water is collected in the trap. 300 mL of water is then added and the butanol is distilled azeotropically. The mixture is cooled and 200 mL of water are added. A resinous product precipitates. The water is decanted and the product dissolved in methyl isobutyl ketone (MIBK) and washed twice with water. The organic phase is dried over sodium sulfate, filtered and rotary evaporated leaving 16 g (79% of theoretical) of a brown resin.

EXAMPLE 13

(Comparative)

Synthesis of N-(3-hydroxyphenyl)-dicyanodiamide (m-HPDICY)

90.6 g of sodium dicyanamide (1.02 mol) and 250 mL of water are added to a 500 mL 3-necked round bottom flask fitted with a reflux condenser, heating mantle and a mechanical stirrer. The mixture is heated to 80° C. at which point all of the dicyanamide salt dissolves. 100.0 g of m-aminophenol (0.916 mol) is added which also dissolves. 76.0 mL of concentrated hydrochloric acid (0.916 mol) is diluted with 80 mL of water and added dropwise over 45 minutes to the solution. A large amount of fine, white solid precipitates and heating is maintained an additional 2.25 hours. The mixture is then allowed to cool, the mixture is filtered and the precipitate is washed with water. The product is recrystallized from 1.5 l of water yielding an offwhite powder which is dried in a vacuum oven. 138 g of product is recovered (85% yield) m.p. 194° C. (lit. m.p. 199°–200° C.). Elemental analysis, found C 55.20%, H 4.76%, N 32.75%, calculated C 54.53%, H 4.59%, N 31.80%.

EXAMPLE 14

Benzyl dicyanodiamide was tested for its solubility in various potential solvents at room temperatures. Increments of 0.5 g each were added to 10 g of the selected solvent until after 10–15 minutes of vigorous stirring the last increment failed to fully dissolve. The results are reported in the following table.

TABLE A

| Solvent | Solubility, g/g |
| --- | --- |
| propylene glycol methyl ether | 0.35 |
| Isopropanol | 0.15 |
| s-butanol | 0.2 |
| n-propanol | 0.15 |
| acetone | 0.65 |
| methyl ethyl ketone | 0.6 |
| ethyl acetate | 0.1 |
| n-butyl acetate | <0.05 |
| toluene | <0.05 |
| ethylene glycol | 0.35 |
| propylene glycol | 0.45 |
| N-methyl pyrrolidone | >0.50 |
| dibutyl ether | 0.125 |
| ethanol | 0.325 |

Methyl benzyl dicyanodiamide also was tested according to the same procedure. Less than 0.50 g was dissolved in acetone and methyl ethyl ketone but 0.15 g was dissolved in propylene glycol methyl ether.

EXAMPLE 15

Solubility testing for substituted cyanoguanidines (dicyanodiamide) was conducted by using a weight ratio of the compound to solvent of 1:10. The sample was agitated slightly and dissolution recorded at 25° C.; complete dissolution receives a rating of +, partial dissolution is +δ, and no dissolution is rated as −. The sample was then heated to 50° C. for 30 minutes and the solubility recorded using the same rating system.

TABLE B

| | Experimental Solubility for Substituted Benzyl-Dicyanodiamides | | | | | | | | | |
| --- | --- | --- | --- | --- | --- | --- | --- | --- | --- | --- |
| | Substituted Benzyl-Dicyanodiamide | | | | | | | | | |
| | BZDICY[a] | | MBZDICY[b] | | MOBZDICY[c] | | DMABZDICY[d] | | HBZDICY[e] | |
| | Temperature (°C.) | | | | | | | | | |
| Solvent | 25 | 50 | 25 | 50 | 25 | 50 | 25 | 50 | 25 | 50 |
| Acetone | + | + | − | + | + | + | − | + | +δ | +δ |
| Methyl ethyl ketone (MEK) | + | + | − | + | + | + | − | + | +δ | +δ |
| 1-Methoxy-2-Propanol | + | + | + | + | + | + | − | + | + | + |
| MEK/1-methoxy-2-propanol (50:50) | + | + | − | + | + | + | − | + | + | + |
| N,N-Dimethylformamide (DMF) | + | + | + | + | + | + | + | + | + | + |
| Dimethyl sulfoxide (DMSO) | + | + | + | + | + | + | + | + | + | + |
| N,N-Dimethylacetamide (DMAC) | + | + | + | + | + | + | − | − | + | + |
| N-Methyl-2-pyrrolidinone (NMP) | + | + | + | + | + | + | + | + | + | + |
| Ethylacetate | − | + | − | − | − | + | − | − | − | − |
| Methanol | + | + | − | + | + | + | − | − | + | + |
| Ethanol | + | + | − | + | + | + | − | − | + | + |

TABLE B-continued

Experimental Solubility for Substituted Benzyl-Dicyanodiamides

| | Substituted Benzyl-Dicyanodiamide | | | | | | | | | |
|---|---|---|---|---|---|---|---|---|---|---|
| | BZDICY[a] | | MBZDICY[b] | | MOBZDICY[c] | | DMABZDICY[d] | | HBZDICY[e] | |
| | Temperature (°C.) | | | | | | | | | |
| Solvent | 25 | 50 | 25 | 50 | 25 | 50 | 25 | 50 | 25 | 50 |
| Toluene | − | − | − | − | − | − | − | − | − | − |

[a] benzyl dicyanodiamide
[b] 4-methyl-benzyl dicyanodiamide
[c] 4-methoxy benzyl dicyanodiamide
[d] 4-(dimethylamino)benzyl dicyanodiamide
[e] 4-hydroxy benzyl dicyanodiamide

TABLE C

Experimental Solubility for Substituted Phenyl-Dicyanodiamides

| | Substituted Phenyl-Dicyanodiamide | | | | | | | | | |
|---|---|---|---|---|---|---|---|---|---|---|
| | PDICY[a] | | m-MPDICY[b] | | p-MPDICY[c] | | m-MOPDICY[d] | | m-HPDICY[e] | |
| | Temperature (°C.) | | | | | | | | | |
| Solvent | 25 | 50 | 25 | 50 | 25 | 50 | 25 | 50 | 25 | 50 |
| Acetone | − | − | − | − | − | − | − | − | − | − |
| Methylethylketone (MEK) | − | − | − | − | − | − | − | − | − | − |
| 1-Methoxy-2-Propanol | − | − | − | − | − | − | − | − | − | + |
| MEK/1-methoxy-2-propanol (50:50) | − | − | − | − | − | − | − | − | − | − |
| N,N-Dimethylformamide (DMF) | + | + | + | + | + | + | + | + | + | + |
| Dimethyl sulfoxide (DMSO) | + | + | + | + | + | + | + | + | + | + |
| N,N-Dimethylacetamide (DMAC) | + | + | + | + | + | + | + | + | + | + |
| N-Methyl-2-pyrrolidinone (NMP) | + | + | − | + | + | + | + | + | − | + |
| Ethylacetate | − | − | − | − | − | − | − | − | − | − |
| Methanol | − | − | − | − | − | − | − | − | − | − |
| Ethanol | − | − | − | − | − | − | − | − | − | − |
| Toluene | − | − | − | − | − | − | − | − | − | − |

[a] phenyl dicyanodiamide
[b] m-methylphenyl dicyanodiamide
[c] p-methylphenyl dicyanodiamide
[d] m-methoxy phenyl dicyanodiamide
[e] m-hydroxy phenyl dicyanodiamide

TABLE D

Experimental Solubility for Substituted Alkyl-Dicyanodiamide

| | Substituted Alkyl-Dicyanodiamide | | | | | |
|---|---|---|---|---|---|---|
| | HXDICY[a] | | DDDICY[b] | | DICY[c] | |
| | Temperature (°C.) | | | | | |
| Solvent | 25 | 50 | 25 | 50 | 25 | 50 |
| Acetone | − | − | − | + | − | − |
| Methylethylketone (MEK) | − | − | − | + | − | − |
| 1-Methoxy-2-Propanol | − | − | − | + | − | + |
| MEK/1-methoxy-2-propanol (50:50) | − | − | − | + | − | +δ |
| N,N-Dimethylformamide (DMF) | + | + | + | + | + | + |
| Dimethyl sulfoxide (DMSO) | + | + | + | + | + | + |
| N,N-Dimethylacetamide (DMAC) | + | + | + | + | +δ | + |
| N-Methyl-2-pyrrolidinone (NMP) | + | + | + | + | + | + |
| Ethylacetate | − | − | − | + | − | − |
| Methanol | − | − | − | + | +δ | + |
| Ethanol | − | − | − | + | − | − |
| Toluene | − | − | − | + | − | − |

[a] hexyl dicyanodiamide
[b] dodecyl dicyanodiamide
[c] dicyanodiamide (cyanoguanidine)

A number of conclusions may be drawn from the data in the foregoing tables. First, in Table D it will be seen that the parent compound, dicyanodiamide or cyanoguanidine, is not soluble in many common and more desirable solvents such as acetone, MEK, and toluene. At room temperature it is partly soluble in methanol but more aggressive solvents such as DMF, DSMO, DMAC, and NMP are needed. These are the solvents currently in use and it has been an objective of the inventors to replace them with more acceptable solvents. Raising the temperature to 50° C. improves the solubility of cyanoguanidine but it is still relatively a difficult compound to dissolve.

Substitution of alkyl chains for one of the amino hydrogens appears to have little effect at least when the chain is only 6 carbons (see hexyl dicyanodiamide, HXDICY). However, when the chain length reaches 12 carbons, the resulting compound is completely soluble in all of the solvents tested at a temperature of 50° C. The solubility at 25° C. is not improved, so that higher temperatures would be necessary in order to use the dodecyl dicyanodiamide (DDDICY), consequently alkyl substitutions are of lesser value compared to benzyl substituted cyanoguanidines.

Table C indicates that despite similarity to benzyl substitutions, substituting a phenyl group for one of the amine hydrogens does not improve the solubility of the cyanoguanidine, nor does substitution of phenyl groups to which are added various other groups have an effect, such as the addition of methyl groups, a methoxy group, or a hydroxy group.

Table B shows that compounds which contain a benzyl group attached to the amino hydrogens provide significantly improved solubility to the cyanoguanidine.

The best solubility is seen with benzyl substituted cyanoguanidine (BZDICY) and a methoxy-substituted benzyl compound (MOBZDICY). Other related compounds are seen to have improved solubility but are somewhat less soluble.

EXAMPLE 16

Part A: 3.10 g of BZDICY was dissolved in 5.60 g of 1-methoxy-2-propanol and heated to 50° C. for 30 minutes with stirring. 0.050 g of 2-Methyl-imidazole (2MI) and 6.92 g of methyl ethyl ketone (MEK) was added to the above solution with stirring.

Part B: 2.0 g of acetone was added to 50.0 g of Dow epoxy 71808 resin (diglycidyl Bisphenol-A (DGEBA) and brominated DGEBA) and mixed well.

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
|---|---|
| 0 | 48 |
| 10 | 78 |
| 20 | 80 |
| 30 | 90 |
| 60 | 93 |
| 90 | 99 |
| 120 | 101 |
| 150 | 104 |
| 180 | 115 |
| 360 | 126 |

The final polymer properties after 360 minutes of cure at 170° C.: Tg by differential scanning calorimeter (DSC)=126° C., Tg by thermomechanical analysis (TMA)=117°±5° C., $\alpha_g = 46 \pm 3$ ppm/°C., $\alpha_{180} = 104 \pm 4$ ppm/°C.

EXAMPLE 17

Part A: 3.10 g of BZDICY was dissolved in 5.60 g of 1-methoxy-2-propanol and heated to 50° C. for 30 minutes with stirring. 0.050 g of Benzyldimethylamine (BDMA) and 6.92 g of methyl ethyl ketone (MEK) was added to the above solution with stirring.

Part B: 2.0 g of acetone was added to 50.0 g of Dow epoxy 71808 resin (diglycidyl Bisphenol-A (DGEBA) and brominated DGEBA) and mixed well.

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
|---|---|
| 0 | 44 |
| 10 | 78 |
| 20 | 79 |
| 30 | 80 |
| 60 | 91 |
| 90 | 96 |
| 120 | 97 |
| 150 | 97 |
| 180 | 101 |
| 360 | 116 |

The final polymer properties after 360 minutes of cure at 170° C.: Tg (DSC)=116° C., Tg (TMA)=108°±9° C., $\alpha_g = 46 \pm 7$ ppm/°C., $\alpha_{180} = 111 \pm 2$ ppm/°C.

EXAMPLE 18

Comparative

Part A: 1.12 g of DICY was dissolved in 6.92 g of Dimethylformamide (DMF) and 5.60 g of 1-methoxy-2-propanol and heated to 50° C. for 30 minutes with stirring. 0.050 g of 2-Methyl-imidazole (2MI) was added to the above solution with stirring.

Part B: 2.0 g of acetone was added to 50.0 g of Dow epoxy 71808 resin (diglycidyl Bisphenol-A (DGEBA) and brominated DGEBA) and mixed well.

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
|---|---|
| 0 | 47 |
| 10 | 80 |
| 20 | 80 |
| 30 | 94 |
| 60 | 95 |
| 90 | 111 |
| 120 | 119 |
| 150 | 120 |
| 180 | 125 |
| 360 | 128 |

The final polymer properties after 360 minutes of cure at 170° C.: Tg (DSC)=128° C., Tg (TMA)=116°±5° C., $\alpha_g = 46 \pm 9$ ppm/°C., $\alpha_{180} = 100 \pm 5$ ppm/°C.

EXAMPLE 19

Comparative

Part A: 1.12 g of DICY was dissolved in 5.20 g of 1-methoxy-2propanol and 6.92 g of DMF heated to 50° C. for 30 minutes with stirring. 0.044 g of 2-Methyl-imidazole (2MI) was added to the above solution with stirring.

Part B: 50.0 g of Dow epoxy 71881 resin (diglycidyl Bisphenol-A (DGEBA) and brominated DGEBA).

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
|---|---|
| 0 | 44 |
| 10 | 80 |
| 20 | 83 |
| 30 | 70 |

-continued

| Time (min.) | Tg (°C.) |
| --- | --- |
| 60 | 83 |
| 90 | 110 |
| 120 | 114 |
| 150 | 116 |
| 180 | 126 |
| 360 | 130 |

The final polymer properties after 360 minutes of cure at 170° C.: Tg (DSC)=130° C., Tg (TMA)=114.8°±4.3° C., $\alpha_g$=34.6±6.6 ppm/°C., $\alpha_{180}$=91.1±5.0 ppm/°C.

EXAMPLE 20

Comparative

Part A: 2.09 g of DICY was dissolved in 5.20 g of 1-methoxy-2-propanol and 6.92 g of DMF heated to 50° C. for 30 minutes with stirring. 0.044 g of 2-Methyl-imidazole (2MI) was added to the above solution with stirring.

Part B: 50.0 g of Dow epoxy 71881 resin (diglycidyl Bisphenol-A (DGEBA) and brominated DGEBA).

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
| --- | --- |
| 0 | 46 |
| 10 | 65 |
| 20 | 66 |
| 30 | 80 |
| 60 | 78 |
| 90 | 94 |
| 120 | 98 |
| 150 | 111 |
| 180 | 118 |
| 360 | 118 |

The final polymer properties after 180 minutes of cure at 170° C.: Tg (DSC)=118° C., Tg (TMA)=120°±3° C., $\alpha_g$=33±7 ppm/°C., $\alpha_{180}$=117±6 ppm/°C.

EXAMPLE 21

Comparative

Part A: 1.67 g of DICY was dissolved in 5.20 g of 1-methoxy-2-propanol and 6.92 g of DMF heated to 50° C. for 30 minutes with stirring. 0.044 g of 2-Methyl-imidazole (2MI) was added to the above solution with stirring.

Part B: 50.0 g of Dow epoxy 71881 resin (diglycidyl Bisphenol-A (DGEBA) and brominated DGEBA).

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
| --- | --- |
| 0 | — |
| 10 | 62 |
| 20 | 69 |
| 30 | 81 |
| 60 | 88 |
| 90 | 93 |
| 120 | 98 |
| 150 | 103 |
| 180 | 110 |
| 360 | 113 |

The final polymer properties after 360 minutes of cure at 170° C.: Tg (DSC)=113° C., Tg (TMA)=124°±5° C., $\alpha_g$=40±3 ppm/°C., $\alpha_{180}$=91±4 ppm/°C.

EXAMPLE 22

Part A: 3.08 g of BZDICY was dissolved in 5.20 g of 1-methoxy-2-propanol and heated to 50° C. for 30 minutes with stirring. 0.044 g of 2-Methyl-imidazole (2MI) and 6.92 g of methyl ethyl ketone (MEK) was added to the above solution with stirring.

Part B: 50.0 g of Dow epoxy 71881 resin (diglycidyl Bisphenol-A (DGEBA) and brominated DGEBA).

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
| --- | --- |
| 0 | 40 |
| 10 | 82 |
| 20 | 87 |
| 30 | 94 |
| 60 | 94 |
| 90 | 90 |
| 120 | 95 |
| 150 | 100 |
| 180 | 100 |
| 360 | 101 |

The final polymer properties after 360 minutes of cure at 170° C.: Tg (DSC)=101° C., Tg (TMA)=102°±5° C., $\alpha_g$=34±3 ppm/°C., $\alpha_{180}$=102±4 ppm/°C.

EXAMPLE 23

Part A: 3.34 g of MBZDICY was dissolved in 5.20 g of 1-methoxy-2-propanol and heated to 50° C. for 30 minutes with stirring. 0.044 g of 2-Methyl-imidazole (2MI) and 6.92 g of MEK was added to the above solution with stirring.

Part B: 50.0 g of Dow epoxy 71881 resin (diglycidyl Bisphenol-A (DGEBA) and brominated DGEBA).

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
| --- | --- |
| 0 | 33 |
| 10 | 89 |
| 20 | 91 |
| 30 | 93 |
| 60 | 103 |
| 90 | 105 |
| 120 | 106 |
| 150 | 112 |
| 180 | 115 |
| 360 | 126 |

The final polymer properties after 360 minutes of cure at 170° C.: Tg (DSC)=126° C., Tg (TMA)=118°±6° C., $\alpha_g 27 \pm 2$ ppm/°C., $\alpha_{180}$=105±2 ppm/°C.

EXAMPLE 24

Part A: 5.78 g of BZDICY was dissolved in 5.20 g of 1-methoxy-2-propanol and heated to 50° C. for 30 minutes with stirring. 0.044 g of 2-Methyl-imidazole (2MI) and 6.92 g of methyl ethyl ketone (MEK) was added to the above solution with stirring.

Part B: 50.0 g of Dow epoxy 71881 resin (diglycidyl Bisphenol-A (DGEBA) and brominated DGEBA).

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
| --- | --- |
| 0 | 43 |
| 10 | 87 |
| 20 | 89 |
| 30 | 85 |
| 60 | 87 |
| 90 | 97 |
| 120 | 101 |
| 150 | 103 |
| 180 | 102 |
| 360 | 113 |

The final polymer properties after 360 minutes of cure at 170° C.: Tg (DSC)=113° C., Tg (TMA)=102°±6° C., $\alpha_g$=47±4 ppm/°C., $\alpha_{180}$=108±4 ppm/°C.

EXAMPLE 25

Part A: 4.62 g of BZDICY was dissolved in 5.20 g of 1-methoxy-2-propanol and heated to 50° C. for 30 minutes with stirring. 0.044 g of 2-Methyl-imidazole (2MI) and 6.92 g of MEK was added to the above solution with stirring.

Part B: 50.0 g of Dow epoxy 71881 resin (diglycidyl Bisphenol-A (DGEBA) and brominated DGEBA).

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
| --- | --- |
| 0 | 41 |
| 10 | 76 |
| 20 | 82 |
| 30 | 81 |
| 60 | 90 |
| 90 | 98 |
| 120 | 100 |
| 150 | 107 |
| 180 | 109 |
| 360 | 113 |

The final polymer properties after 360 minutes of cure at 170° C.: Tg (DSC)=113° C.

EXAMPLE 26

Part A: 3.10 g of BZDICY was dissolved in 5.60 g of 1-methoxy-2-propanol and heated to 50° C. for 30 minutes with stirring. 0.044 g of Benzyldimethylamine (BDMA) and 6.92 g of methyl ethyl ketone (MEK) was added to the above solution with stirring.

Part B: 50.0 g of Dow epoxy 71881 resin (diglycidyl Bisphenol-A (DGEBA) and brominated DGEBA).

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
| --- | --- |
| 0 | 31 |
| 30 | 60 |
| 60 | 98 |
| 90 | 108 |
| 120 | 112 |
| 150 | 117 |
| 180 | 124 |
| 360 | 122 |

The final polymer properties after 360 minutes of cure at 170° C.: Tg (DSC)=122° C., Tg (TMA)=103°±3° C., $\alpha_g$=39±5 ppm/°C., $\alpha_{180}$=102±4 ppm/°C.

EXAMPLE 27

Part A: 3.10 g of BZDICY was dissolved in 5.60 g of 1-methoxy-2-propanol and heated to 50° C. for 30 minutes with stirring. 0.044 g of 4-(dimethylamino)-N,N-dimethylbenzylamine (DMBDMA) and 6.92 g of MEK was added to the above solution with stirring.

Part B: 50.0 g of Dow epoxy 71881 resin (diglycidyl Bisphenol-A (DGEBA) and brominated DGEBA).

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
| --- | --- |
| 0 | 25 |
| 30 | 46 |
| 60 | 89 |
| 90 | 111 |

| Time (min.) | Tg (°C.) |
|---|---|
| 120 | 113 |
| 150 | 116 |
| 180 | 117 |
| 360 | 117 |

The final polymer properties after 360 minutes of cure at 170° C.: Tg (DSC)=117° C., Tg (TMA)=104°±3° C., $\alpha_g$=46.95±2.7 ppm/°C., $\alpha_{180}$=107.9±2.2 ppm/°C.

EXAMPLE 28

Part A: 3.62 g of MOBZDICY was dissolved in 5.20 g of 1-methoxy-2-propanol and heated to 50° C. for 30 minutes with stirring. 0.044 g of 2-Methyl-imidazole (2MI) and 6.92 g of methyl ethyl ketone (MEK) was added to the above solution with stirring.

Part B: 50.0 g of Dow epoxy 71881 resin (diglycidyl Bisphenol-A (DGEBA) and brominated DGEBA).

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
|---|---|
| 0 | 43 |
| 10 | 86 |
| 20 | 87 |
| 30 | 91 |
| 60 | 90 |
| 90 | 106 |
| 120 | 107 |
| 150 | 109 |
| 180 | 115 |
| 360 | 125 |

The final polymer properties after 360 minutes of cure at 170° C.: Tg (DSC)=125° C., Tg (TMA)=109°±3° C., $\alpha_g$=39±8 ppm/°C., $\alpha_{180}$=100±3 ppm/°C.

EXAMPLE 29

Part A: 3.86 g of DMABZDICY was dissolved in 5.20 g of 1-methoxy-2-propanol and heated to 50° C. for 30 minutes with stirring. Then 6.92 g of MEK was added to the above solution with stirring.

Part B: 50.0 g of Dow epoxy 71881 resin (diglycidyl Bisphenol-A (DGEBA) and brominated DGEBA).

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
|---|---|
| 0 | 54 |
| 30 | 86 |
| 60 | 93 |
| 90 | 108 |
| 120 | 110 |
| 150 | 114 |
| 180 | 119 |
| 360 | 125 |

The final polymer properties after 360 minutes of cure at 170° C.: Tg (DCS)=125° C., Tg (TMA)=104°±5° C., $\alpha_g$=45±7 ppm/°C., $\alpha_{180}$=104±2 ppm/°C.

EXAMPLE 30

Part A: 3.86 g of DMABZDICY was dissolved in 5.20 g of 1-methoxy-2-propanol and heated to 50° C. for 30 minutes with stirring. 0.044 g of 2-Methyl-imidazole (2MI) and 6.92 g of methyl ethyl ketone (MEK) was added to the above solution with stirring.

Part B: 50.0 g of Dow epoxy 71881 resin (diglycidyl Bisphenol-A (DGEBA) and brominated DGEBA).

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
|---|---|
| 0 | 46 |
| 30 | 93 |
| 60 | 98 |
| 90 | 110 |
| 120 | 114 |
| 150 | 120 |
| 180 | 120 |
| 360 | 125 |

The final polymer properties after 360 minutes of cure at 170° C.: Tg (DSC)=125° C., Tg (TMA)=128°±7° C., $\alpha$=42±9 ppm/°C., $\alpha_{180}$=126±15 ppm/°C.

EXAMPLE 31

Part A: 4.60 g of BZDICY was dissolved in 5.60 g of 1-methoxy-2-propanol and heated to 50° C. for 30 minutes with stirring. 0.090 g of 1-(2-cyanoethyl)-2-ethyl-4-methylimidazole (CEM) was added to the above solution with stirring.

Part B: 50.0 g of Dow epoxy 71881 resin (diglycidyl Bisphenol-A (DGEBA) and brominated DGEBA).

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
|---|---|
| 0 | 23 |
| 10 | 80 |
| 20 | 90 |
| 30 | 90 |
| 60 | 96 |
| 90 | 100 |
| 120 | 110 |
| 150 | 115 |
| 180 | 116 |

-continued

| Time (min.) | Tg (°C.) |
|---|---|
| 360 | 120 |

The final polymer properties after 360 minutes of cure at 170° C.: Tg (DSC)=120° C., Tg (TMA)=122°±2° C., $\alpha_g=34\pm5$ ppm/°C., $\alpha_{180}=92\pm5$ ppm/°C.

EXAMPLE 32

Part A: 2.40 g of BZDICY was dissolved in 12.60 g of 1-methoxy-2-propanol and heated to 50° C. for 30 minutes with stirring. 0.15 g of 2-Methyl-imidazole (2MI) and 15.50 g of methyl ethyl ketone (MEK) was added to the above solution with stirring.

Part B: 69.50 g of Dow epoxy 71881 resin (diglycidyl Bisphenol-A (DGEBA) and brominated DGEBA).

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
|---|---|
| 0 | 36 |
| 30 | 80 |
| 60 | 84 |
| 90 | 107 |
| 120 | 117 |
| 150 | 119 |
| 180 | 124 |
| 360 | 129 |

The final polymer properties after 360 minutes of cure at 170° C.: Tg (DSC)=129° C., Tg (TMA)=102°±2° C., $\alpha_g=42\pm11$ ppm/°C., $\alpha_{180}=107\pm7$ ppm/°C.

EXAMPLE 33

Part A: 3.38 g of HBZDICY was dissolved in 5.20 g of 1-methoxy-2-propanol and heated to 50° C. for 30 minutes with stirring. 0.044 g of 4-(dimethylamino)-N,N-dimethylbenzylamine (DMBDMA) and 6.92 g of MEK was added to the above solution with stirring.

Part B: 50.0 g of Dow epoxy 71881 resin (diglycidyl Bisphenol-A (DGEBA) and brominated DGEBA).

Part A and Part B were mixed together and allowed to age for 24 hours. The resin varnish was then B-Staged on a hot plate in a thin casting pan. The B-Staged resin was ground into fine powder and then cured at 170° C. in a hydraulic press at 1379 kPa. The polymer had the following properties as a function of cure.

| Time (min.) | Tg (°C.) |
|---|---|
| 0 | 34 |
| 30 | 90 |
| 60 | 82 |
| 90 | 113 |
| 120 | 120 |
| 150 | 121 |
| 180 | 123 |
| 360 | 127 |

The final polymer properties after 360 minutes of cure at 170° C.: Tg (DSC)=127° C., Tg (TMA)=112°±1° C., $\alpha_g=53\pm4$ ppm/°C., $\alpha_{180}=126\pm6$ ppm/°C.

EXAMPLE 34

Two substituted cyanoguanidines, N-Benzyl-dicyanodiamide (BZDICY and N-(4-Methylbenzyl)-dicyanodiamide (MBZDICY), were used to prepare epoxy laminates. Four accelerators were tested for each of the two cyanoguanidines. Formulations using Dow 71881 epoxy resins were compounded with 7.75 parts of BZDICY for 100 parts of epoxy or 8.37 parts of MBZDICY per 100 parts of epoxy. The BZDICY and MBZDICY were dissolved in a solvent mixture of 4 parts propylene glycol methyl ether and 5 parts MEK. The accelerators were added until a 150 second gel time was obtained when a sample was heated on a hot plate at 171° C. Laminates were then prepared using the resin formulations by coating the resins onto type 1080-307 glass fabric (supplied by Clark-Schwebel). Samples of laminates 305 mm×305 mm were made using 2 plies of the resin coated fabric. These were converted to a prepreg by curing in hot air for 2 to 8 minutes at 177° C. Final curing to a finished laminate was carried out by applying pressure of 2068 kPa (gauge) during a heating cycle including a rise up to 176.6° C., maintaining at 176.6° C. for 50 minutes, and then cooling to 20° C. over 15 minutes. The resulting laminates were tested for properties related to their performance as electronic circuit boards and compared with similar laminates made using dicyanodiamide (cyanoguanidine). The results of these tests are summarized in the following table.

TABLE E

|  | Control A[1] | Control B[2] | BZDICY Accelerators | | | | MBZDICY Accelerators | | | |
|---|---|---|---|---|---|---|---|---|---|---|
|  |  |  | CDI[3] | DMAP[4] | 2MI[5] | 2PI[6] | CDI | DMAP | 2MI | 2PI |
| Water Absorption, wt. %[7] | 2.76 | 2.82 | 3.08 | 3.29 | 2.82 | 2.5 | 2.39 | — | 2.44 | 3.04 |
| Arc Resistance, sec[8] | N/A | 84 | 75 | 73 | N/A | 69 | 86 | — | 64 | 81 |
| H$_2$SO$_4$ Etchability wt. %[9] | 9.35 | 12 | 12.9 | 12.3 | 14 | 9.12 | — | — | — | — |
| MeCL$_2$ Absorption wt. %[10] | 12.7 | 7.79 | 13.87 | 15.11 | 13.14 | 12.36 | 9.84 | — | 11 | 11 |
| Tg-DSC[11], °C. | 131 | 135 | 124 | 125 | 125 | 125 | 124 | 123 | 124 | 125 |
| Peel Strength A[12] | 57.9/73.8 | 69.6/71.7 | 71.7/75.2 | 73.8/71.7 | 75.8/77.2 | 66.9/59.3 | 75.8/71.7 | 71.0/75.2 | 72.3/75.8 | 75.8/75.8 |
| Peel Strength E[13] | 57.9/66.2 | 63.4/61.4 | 65.5/66.2 | 62/62 | 59.3/58.6 | 45.5/45.5 | 82/84.1 | 54.5/68.9 | 50.3/55.8 | 64.1/68.9 |
| Solder Blister | 43 | 21 | 44 | 18 | 74 | 54 | 75 | 13 | 83 | 77 |

TABLE E-continued

| | | BZDICY Accelerators | | | | MBZDICY Accelerators | | | |
|---|---|---|---|---|---|---|---|---|---|
| Control A[1] | Control B[2] | CDI[3] | DMAP[4] | 2MI[5] | 2PI[6] | CDI | DMAP | 2MI | 2PI | sec[14]

[1] 100 parts Dow 2483, 2.8 parts dicyanodiamide, 0.08 parts 2-methyl-imidazole
[2] 100 parts Dow 71881, 2.8 parts dicyanodiamide, 0.08 parts 2-methyl-imidazole
[3] 1,1'-carbonyldiamidazole
[4] 2-Dimethylaminopyridine
[5] 2-methyl-imidazole
[6] 2-phenyl-imidazole
[7] 24 hours in boiling water (100° C.)
[8] seconds to failure after conditioning for 48 hours in 50° C. water (ASTM 2.5.1)
[9] percent weight loss after 30 seconds in concentrated $H_2SO_4$ at room temperature
[10] percent weight gain after 20 minute submersion at room temperature
[11] glass transition temperature by differential scanning calorimeter method
[12] kPa at room temperature
[13] kPa after 1 hour at 125° C.
[14] time to failure in 550° C. solder bath From the above results it was concluded that 2-methyl-imidazole and 1,1'-carbonyldiamidazole were preferred of the accelerators tested. Both BZDICY and MBZDICY were considered to perform as well as dicyanodiamide in the Control samples and since the substituted cyanoguanidines permit the use of more acceptable solvents, they have an important advantage over dicyanodiamide (cyanoguanidine).

EXAMPLE 35

Synthesis of 1-Phenethyl-3-cyanoquanidine (PEDICY)

48.25 g (0.398 moles) of phenethyl amine is charged to a 500 mL three-neck round bottom flask equipped with a stirring shaft and a dropping funnel. The flask is cooled in an ice bath as 38.59 g (0.398 moles) of concentrated hydrochloric acid is added dropwise. After the addition of the acid, the ice bath is replaced by a heating mantle and the mixture is heated to 50° C. 37.20 g (0.418 moles) of sodium dicyanamide is added to the flask with stirring. The mixture is heated to 100° C. and stirred for 6.5 hours then cooled in an ice bath. 150 mL of water are added and the white, crystalline precipitate is collected on a Buchner funnel. The product is recrystallized from water yielding 55.5 g of 1-phenethyl-3-cyanoguanidine (74.1% of theoretical) melting point at 111°–112° C.

EXAMPLE 36

Solubility of 1-Phenethyl-3-cyanoguanidine (PEDICY)

0.1 g. portions of phenethyl dicy (PEDICY) were weighed into vials and 1 mL of the following solvents were added: acetone, methyethylketone, N,N-Dimethylformamide (DMF), N,N-Dimethylacetamide (DMAc), N-Methyl-2-pyrrolidinone (NMP) ethyl acetate (EtAc), methanol, ethanol and toluene. Table F is a tabulation of the solubility at 25° C. and 50° C., a + rating notes solubility in the solvent and a — rating notes no solubility in the solvent.

TABLE F

| | PEDICY | |
|---|---|---|
| Solvent | 25° C. | 50° C. |
| Acetone | + | + |
| MEK | + | + |
| DMF | + | + |
| DMAc | + | + |
| NMP | + | + |
| EtAc | — | + |
| Methanol | + | + |
| Ethanol | + | + |
| Toluene | — | — |

EXAMPLE 37

Epoxy curing with 1-Phenethyl-3-cyanoguanidine 1.86 g. of 1-phenethyl-3-cyanoguanidine (PEDICY) was dissolved in 25 mL of acetone. 0.11 g of 2-methylimidazole were added and the mixture stirred until solubilized.

This solution was added to 51.25 g of Dow epoxy XU 71881 resin (diglycidyl Bisphenol A (DGEBA) and brominated DGEBA) and stirred until a homogeneous solution was obtained. This solution was B-Staged on a hot plate in a thin casting pan. The B-Staged resin was ground into a fine powder and cured at 170° C. in a hydraulic press at 1379 kPa for 15 minutes. Post cure was achieved in a 170° C. convection oven.

The polymer had the following properties as a function of cure:

| Time | Tg (°C.) |
|---|---|
| 60 | 104.9 |
| 180 | 123.2 |
| 360 | 126.6 |

EXAMPLE 38

Synthesis of N-Benzyl-dicyandiamide (BZDICY)

46.8 mL (0.43 moles) of benzylamine are charged into a one liter three necked flask fitted with a mechanical stirrer, thermometer and addition funnel. The flask is placed in an ice bath and the amine is cooled to 10° C. 34.8 mL of 37% hydrochloric acid (0.42 moles) are added dropwise to the stirred amine. The temperature climbs slowly to 60° C. at the completion of the neutralization. The ice bath is removed and a heating mantle is brought into place. The temperature is raised to 70° C. and 39.0 g of 96% sodium dicyanamide is added to the reactor. The temperature is then quickly raised to 108° C. and the mixture stirred at this temperature for 1.5 hours. 200 mL of water are then added to the reactor and the mixture cooled to ambient temperature with stirring. A white precipitate forms on cooling which is collected on a Buchner funnel. This solid is washed twice with 150 mL portions of 5% acetic acid (aqueous) and twice with 150 mL portions of water and is then dried under vacuum. 54.1 g of N-benzyl-dicyandiamide (74% of theoretical) melting at 111.6° C. was recovered.

We claim:

1. A one-part epoxy resin composition curing at temperatures above ambient consisting essentially of an epoxy resin and a substituted cyanoguanidine latent curing agent for said epoxy resin and soluble therein and having improved solubility for organic solvents relative to cyanoguanidine and having the formula

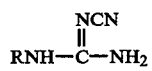

where R is —CH$_2$C$_6$H$_4$X or —CH$_2$CH$_2$C$_6$H$_4$X
and X is —H, —CH$_3$, —OCH$_3$, —OH, or —NY$_2$ and Y is —H, or —CH$_3$ and optionally a catalyst.

2. The composition of claim 1 wherein R is —CH$_2$C$_6$H$_4$X.

3. The composition of claim 2 wherein X is hydrogen.

4. The composition of claim 2 wherein X is a methyl group.

5. The composition of claim 2 wherein X is a methoxy group.

6. The composition of claim 2 wherein X is a dimethylamino group.

7. The composition of claim 1 wherein R is —CH$_2$CH$_2$C$_6$H$_4$X.

8. The composition of claim 7 wherein X is hydrogen.

9. The composition of claim 7 wherein X is methyl group.

10. The composition of claim 7 wherein X is a methoxy group.

11. The composition of claim 7 wherein X is dimethylamino group.

* * * * *